United States Patent [19]

Ferstandig

[11] 4,138,355
[45] Feb. 6, 1979

[54] FLUORINE SUBSTITUTION IN 1,1,1-TRIHALOMETHANES

[75] Inventor: Louis L. Ferstandig, Ridgewood, N.J.

[73] Assignee: Halocarbon Products Corporation, Hackensack, N.J.

[21] Appl. No.: 853,695

[22] Filed: Nov. 21, 1977

Related U.S. Application Data

[60] Division of Ser. No. 712,401, Aug. 10, 1976, Pat. No. 4,078,007, which is a continuation-in-part of Ser. No. 619,534, Oct. 3, 1975, abandoned.

[51] Int. Cl.$^2$ .................. C07C 19/08; C23F 11/18
[52] U.S. Cl. ............................ 252/182; 134/41; 252/149; 252/387; 422/12
[58] Field of Search ............. 252/182, 387, 147; 21/2.5 R, 2.7 R; 134/2, 28, 41; 423/491

[56] References Cited

U.S. PATENT DOCUMENTS

| | | | |
|---|---|---|---|
| 3,087,778 | 4/1963 | Negra et al. | 252/387 |
| 3,223,626 | 12/1965 | Murphy et al. | 252/387 |
| 3,808,140 | 4/1974 | Mago | 252/387 |

Primary Examiner—Benjamin R. Padgett
Assistant Examiner—Irwin Gluck

Attorney, Agent, or Firm—Sprung, Felfe, Horn, Lynch & Kramer

[57] ABSTRACT

Fluorine is substituted for other halogen atoms on the 1-carbon atom of a compound which contains a 1,1,1-trihalomethyl group (trichloromethyl) by contacting said compound or a precursor thereof with liquid HF in the presence of a mixture of antimony pentahalide with a least an approximately equimolar amount of antimony trihalide. The antimony halides may be added as the chlorides and in situ converted to fluorides and/or chlorofluorides, which are believed to be the essential agents. Additional starting material and antimony pentahalide may be added in the course of the reaction which proceeds stepwise. When the reactant is 1,1,1,3-tetrachloropropane the reaction can be continued to produce 3-chloro-1,1,1-trifluoropropane which, upon reaction with alkali, yields 3,3,3-trifluoropropene, of known utility in making fluorosilicones. The reaction is also useful in the production of 2-chloro-1,1,1-trifluoroethane from 2-chloro-1,1,1-trihaloethanes and/or precursors thereof such as trichloroethylene, as well as in the production of trifluoromethane and chlorotrifluoromethane from chloroform and carbon tetrachloride, respectively.

1 Claim, No Drawings

FLUORINE SUBSTITUTION IN 1,1,1-TRIHALOMETHANES

This is a division, of application Ser. No. 712,401, filed Aug. 10, 1976, now U.S. Pat. No. 4,078,007, which was a continuation-in-part of Ser. No. 619,534, filed Oct. 3, 1975, now abandoned.

The present invention relates to the replacement of other halogen atoms in organic compounds by fluorine.

Fluorine-containing alkanes and alkenes are well-known in the literature and have a variety of end uses. Fluoroalkanes are useful in anesthesiology and as intermediates for various chemical reactions, including making fluoroalkenes. The alkenes can be silylated to produce fluorosilicones, according to Belgian Pat. No. 647,975, which silicones are of marked chemical resistance, i.e. inert, rendering them especially suited for fabricating resistant articles, such as gaskets, liners, and the like, if solid, or, if liquid, suitable for functional fluids.

Production of 1,1,1-trifluoropropene, for example, proceeds as follows starting with 1,1,1,3-tetrachloropropane (TCP):

$$CCl_3CH_2CH_2Cl + 3HF \leftarrow CF_3CH_2CH_2Cl + 3 HCl \quad (I)$$

$$CF_3CH_2CH_2Cl + NaOH \leftarrow CF_3CH=CH_2 + NaCl + H_2O \quad (II)$$

The reaction with HF, however, is difficult, slow and low in yield.

The art reports various attempts to effect reaction I using antimony halides, e.g. antimony dichlorotrifluoride and trifluoride, as the florinating agent in place of HF, viz. Henne JACS Vol. 73 (1951) 1042, and Haszeldine JCS (1953) 3371ff, especially 3374. These processes, however, have also been slow, low in yield, costly, necessitated use of inert organic solvents to suspend the antimony salts and/or have been difficult to reproduce.

It is accordingly an object of the invention to provide a process for replacing other halogen atoms of a 1,1,1-trihalomethane with fluorine in a simple, efficient manner.

These and other objects and advantages are realized in accordance with one aspect of the present invention pursuant to which a 1,1,1-trihalomethane is contacted with liquid HF in the presence of a mixture of antimony pentahalide with at least an approximately equimolar amount of antimony trihalide, whereby the 1-halogen atoms are selectively and stepwise replaced by fluorine; as employed herein, approximately equimolar embraces 1:1 ± about 10%. If the 1,1,1-trihalomethane also carried one or two other halogen atoms such as chlorine or bromine on the 3-carbon atom or other carbon atom which also carried at least one hydrogen atom, such other halogen atoms would be unattacked while the 1-halogen atoms were being replaced. Thus employing TCP as the 1,1,1-trihalomethane starting material the reactions can be schematically represented as follows:

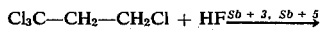

$$Cl_3C-CH_2-CH_2Cl + HF \xrightarrow{Sb+3, Sb+5}$$

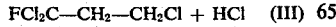

$$FCl_2C-CH_2-CH_2Cl + HCl \quad (III)$$

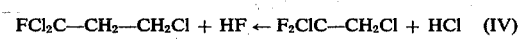

$$FCl_2C-CH_2-CH_2Cl + HF \leftarrow F_2ClC-CH_2-CH_2Cl + HCl \quad (IV)$$

$$F_2ClC-CH_2-CH_2Cl + HF \leftarrow F_3C-CH_2-CH_2Cl + HCl \quad (V)$$

The reaction can be terminated prior to the last indicated step and mixtures of products can be obtained and fractionated to recover any of the organic products of (III), (IV) and (V).

Preferred antimony pentahalides and triahlides are the fluorides and chlorofluorides. Fluorides and chlorofluorides may be formed in situ from the corresponding antimony chlorides, the HF being employed in sufficient amount to effect their formation advantageously with a slight excess. It is believed the antimony pentahalide and triahalide form a 1:1 complex and it may be the complex which is the active catalyst. The mixture comprising the complex and/or pentahalide plus excess trihalide can be formed by addition of the components in the desired proportions or it can be formed by addition of only one component, or of both components in proportions different from that desired, and one component can be converted in situ to the other to establish the intended proportion. Thus, if only antimony pentahalide were added, a reducing agent such as an olefin (which itself could be formed in situ) or a metal could be used to convert some of the pentahlide to the trihalide and thereby establish the desired proportion. Alternatively, if only trihalide is added, an oxidizing agent such as bromine or chlorine could be used to convert less than half the trihalide to pentahalide, again establishing the desired proportion, then adding the HF.

If the ratio of antimony trihalide:antimony pentahalide is less than 1, the 1:1 complex is still believed to form but it diluted with excess antimony pentahalide. Accordingly, to that extent it will suffer the disadvantages attending free antimony pentahalide as the catalyst, viz. replacement of hydrogen by halogen plus corrosion.

The temperature of the reaction is not critical although higher temperatures will, of course, speed up the reaction. There is no need to go below room temperature which woul require cooling. Similarly temperatures above 100° C. generate unduly high pressures so a temperature of about 0° to 100° C. is suitable, preferably about 30°–75° C.

Since HCl boils at −35° C. and HF at 19° C., the process is desirably run under pressure, e.g. about 20 to 200 psig, preferably about 70 to 100 psig; thereby the HCl can be removed by distillation at convenient reflux temperatures while leaving behind the HF.

In accordance with one preferred aspect of the invention, the reactant is TCP as illustrated above, and the reaction proceeds stepwise replacing one chlorine atom at a time to an ultimate product which is 3-chloro-1,1,1-trifluoropropane (TFCP). If this same reactant is contacted with antimony trihalide in the absence of HF and antimony pentahalide, no reaction ensues. If HF is added, reaction proceeds to a small degree. If antimony trifluoride is employed in admixture with antimony pentachloride, according to Cavlin et al, J. Org. Chem. 21 (1956) 1342–1347, some desired product is produced but a side reaction ensues with the evolution of HCl, presumably in part according to the equation

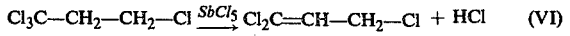

$$Cl_3C-CH_2-CH_2-Cl \xrightarrow{SbCl_5} Cl_2C=CH-CH_2-Cl + HCl \quad (VI)$$

This is also the result if the halogenating agent is antimony pentafluoride alone. The olefins thus produced form byproduct polymers which are black, resinous and represent a significant loss in yield. If HF is added to antimony pentafluoride, the reaction proceeds somewhat better but substantial resinous by-product is still produced. Even more troublesome, antimony pentafluoride or pentachloride plus HF are extremely corresive to most metals and the expensive equipment is rapidly consumed.

The antimony fluorides appear to be active reactants but antimony can be added as the chloride salts and the HF will convert them to antimony fluorides and HCl gas. As the antimony fluorides react with the organic chlorides the antimony salts are converted to the mixed chloro-fluoro salts which are still catalysts for this process. The chloro-fluoro salts, however, react repeatedly with excess HF to form fluorides and HCl again. If the HF content is allowed to drop so that the antimony salts have very low fluoride content, then catalytic activity diminishes.

As noted, pentavalent salts appear to be reduced during the reaction, perhaps by corrosion of the metal vessel or by reaction with organic reducing agents. As this happens the catalytic activity diminishes and finally stops. Pentavalent antimony can be added at this point, keeping the overall ratio of pentavalent to trivalent (including that formed by earlier reduction of pentavalent) in the desired range.

At the start of a cycle, the antimony salts generally range from about 5 to 35%, and preferably from about 8 to 20%, by weight of HF plus antimony salts. The antimony salt contant rises as the reaction proceeds due to consumption of HF and addition of increments of antimony salts.

The timing of the addition of pentavalent antimony to the mixture to replenish catalytic activity is important. As shown in Example 10 hereinbelow, SbCl$_5$ reacts violently with 1,1,3-trichloro-1-fluoropropane (HFCP) and TCP and as Example 5 shows, yields are lowered by addition of SbCl$_5$ to poorly converted mixtures, i.e. where the reactions (IV) and (V) have not occurred to an appreciable extent. The preferred way to avoid these problems is to moniter the extent of reaction and thereby limit or step the TCP addition as the catalytic diminishes. It is desirable to stop the TCP addition when the catalyst remaining will in a short time convert all the TCP in the mixture to about 90% TFCP and 10% 1,3-dichloro-1,1-difluoropropane (DFCP). Lower reaction extents, i.e. where the mixture contains about 5% HFCP, are much less desirable for the above reasons.

It appears that, after SbCl$_5$ has been added to the mixture and allowed to react with HF and the trivalent antimony present, the MFCP and TCP decomposition does not occur.

One practical way of proceeding, exemplified hereinbelow, involved the following steps:

1. Put HF in a steel reactor in the full amount desired.
2. Premix SbCl$_5$ and SbCl$_3$ in 1:1 molar ratio and add to the reaction as a melt.
3. Add a quantity of TCP such that it is converted to about 90% TFCP and 10% DPCF (see Example 14).
4. Then add a further charge of SbCl$_5$ and an additional quantity of TCP.
5. Steps 3 and 4 are repeated until the mixture contains about 2 to 8 wt. % of HF.
6. Separate the mixture to recover the TFCP product.

The crude product even without purification is directly suited for reaction with an alkali according to equation II illustrated hereinabove.

As noted, the reaction is generally applicable to trihalomethanes which is also intended to include precursors thereof, although some compounds react better than others. Thus the reactant may be a 1,1,1-trihaloalkane or 1,1,1-trihalomethyl benzene, e.g. the trihalomethyl or equivalent moiety may be connected to hydrogen (trihalomethane); to halogen (carbon tetrachloride); to an alkyl radical, especially a lower alkyl radical having up to 4 carbon atoms, e.g. ethyl (1,1,1-trihalopropane) or methyl (1,1,1-trihaloethane); to a halogen-substituted alkyl radical, especially a lower alkyl radical having up to 4 carbon atoms and 1 or more chlorine, bromine and/or fluorine atoms, e.g. chloromethyl (2-chloro-1,1,1-trifluoroethane) or 2-chloroethyl (1,1,1,3-tetrachloropropane); to an aromatic radical especially one having from 6 to 10 carbon atoms such as phenyl (benzotrichloride) or phenylene (hexachloroxylene), halogen substitution products thereof, and the like.

It is also applicable to precursors thereof such as trichloroethylene which in the instant system with the hydrogen fluoride forms 1,1,2-trichloro-1-fluoroethane. For certain reasons not fully understood, certain other structures on the molecule have a somewhat inhibitory effect in that longer times may be required or lower yields produced, e.g. two fluorine atoms on a carbon adjacent the trihalomethyl group such as in CF$_2$BrCF$_2$CH$_2$CH$_2$Br. Also CCl$_3$CH$_2$CH$_2$CH$_2$Cl is somewhat less reactive than TCP, for example.

In practice, the last chlorine atom of a trichloromethane is the most difficult to replace with fluorine. Consequently if a reaction product contains a mixture of several compounds but a substantial proportion is 1,1,1-trifluorinated it is an indication the reaction was stopped a little too soon since the system is obviously capable of producing the desired product. Similarly, a quick test for operability and conditions can involve the 1-chloro-1,1,1-difluoromethyl compound as starting material. If it is readily converted to the 1,1,1-trifluoromethyl counterpart it is an indication that the reaction starting from the 1,1,1-trichloromethyl counterpart would also proceed easily.

The invention is further described in the following illustrative examples wherein all parts are by weight unless otherwise expressed.

EXAMPLE 1

Thirty-three pounds of HF was placed in a jacketed monel 10 gallon autoclave equiped with a column with a refrigerant-cooled condenser, stirrer, and lines for adding to and sampling the contents of the vessel. The HF was heated to 50° C. and then 8.7 lbs. of a molten mixture containing 91 mole % SbCl$_3$ and 9 mole % SbCl$_5$ was added. There was a small immediate pressure rise due to the fluorination of the antimony salts and the formation of HCl. Nineteen pounds of a mixture containing equal amounts of TFCP and DFCP was added rapidly while the mixture was kept at 50° C. of 1 hour and then at 70°–80° C. for 2 hours. During this time HCl was distilled out as formed. The distillation was continued, lowering the pressure to atmospheric until the overhead temperature was in the region of 10° to 20° C. indicating that a mixture of the organic product and HF was refluxing. A portion of the refluxing condensate was allowed to stratify, the lower organic layer removed and the upper HF layer was returned to the column. The organic material recovered was 98% and the yield was 89% of the theory.

EXAMPLE 2

To the HF and antimony salts remaining in the autoclave from Example 1 were added 24 lbs. of TCP in 12 hours while keeping the reactor at 50° C. and removing the HCl as formed. The reaction was heated for an additional hour at 50° C. and an additional 4 hours at 75 to 80° C., after which a distillation-separation as described in Example 1 gave a mixture which was 23% TFCP and 72% DFCP with a yield of 87% of theory. This shows the diminishing activity of the catalyst presumably due to reduction in the proportion of pentavalent antimony as the reaction proceeded.

EXAMPLE 3

To the mmixture remaining in the reactor from Example 2, 1 lb. of $SbCl_5$ was added and then the organic product of Example 2 was fed back to the vessel. The HCl was distilled off and the distillation-separation was performed, giving a product which was 99.7% TFCP, yield 93% of theory. Thus, as the pentavalent antimony proportion was raised relative to the amount present at the end of Example 2, the activity of the catalyst was also raised.

EXAMPLE 4

Using the vessel and procedures described in Example 1 the following reactants and quantities were mixed: HF 29.75 lbs., antimony chlorides 2.5 lbs., 46 mole % tri and 54% penta, TCP 25 lbs. After reacting for 17.5 hours at about 50° C, the separated organic material was 90% TFCP and 10% DFCP in essentially theoretical yield. This shows that minor deviations from the minimum equimolar trivalent:pentavalent antimony are permissible.

EXAMPLE 5

To the mixture remaining in the reactor from Example 4, 21 lbs. of TCP was added at 50° C over a 5.6 hour period. An insufficient amount of HCl was evolved, indicating an incomplete fluorination. Antimony pentachloride (0.625 lb.) was added giving an extremely rapid HCl evolution. Another 20 lbs. of TCP was then added again, resulting in insufficient HCl production. Once again $SbCl_5$ (1.5 lbs.) was added, giving rise to immediate HCl evolution. Analysis of the reactor contents indicated that a large amount of non-volatile residues and only a low yield of TFCP and DFCP were formed.

EXAMPLE 6

Twenty-two pounds of HF and 2 lbs. of $SbCl_3$ and $SbCl_5$ mixture, 57 and 43 mole % respectively, were mixed in the same manner as in Example 1. Six pounds of TCP was then added at 50° C. and the HCl was eliminated as formed. Then about 0.1 lb. of $SbCl_5$ was added, followed by 10 lbs. of TCP. The steps of adding small amounts (0.1 to 0.6 lb.) of $SbCl_5$ followed by increments of TCP of 5 to 10 lbs. were repeated until a total of 56 lbs. of TCP had been added. The distillation-separation yielded a mixture of 74% TFCP, 18% DFCP, 8% MFCP and trace TCP in 98% of theory.

EXAMPLE 7

In an experiment similar to Example 6 the final product and HF were co-distilled from the reaction mixture without separation. The distillate was then cooled in a Dry Ice-trichloroethylene bath and the layers separated. Each layer was contaminated with only small amounts of the other layer.

EXAMPLE 8

Using the same vessel as Example 1, 11 lbs. of $SbCl_5$ was added to 33 lbs. of HF at about 23° C. Then while maintaining the temperature at 23° to 35° C, 6.6 lbs. of TCP was added, the HCl was removed and the organic product was recovered by distillation-separation. The organic yield was 99% pure TFCP but only 34% of theory. This shows that too high a ratio of pentavalent:trivalent antimony (initially ∞, diminishing somewhat during the reaction) resulted in low yield.

EXAMPLE 9

Using the residue in the reactor from Example 8, 33.5 lbs. of TCP was added. The reaction and distillation were carried out so that the temperature was mostly at 20° C. but always in the range of 18° to 38° C. The distillation-separation product was 99.6% TFCP in a yield of 95% of theory. This shows that the pentavalent:trivalent antimony ratio in the mass at the end of Example 8 had been reduced to a level where conversions were substantially complete and quantitative.

EXAMPLE 10

In a test tube several grams of MFCP was added to a small quantity of $SbCl_5$. There was an immediate evolution of HCl and the mixture turned black and viscous. TCP reacted similarly. Mixtures of $SbCl_5$ and $SbCl_3$ produced the same result.

EXAMPLE 11

A series of test metal strips were placed in the autoclave described in Example 1 during a series of TCP fluorinations at 50° C. where the initial $Sb^{+5}$ to $Sb^{+3}$ mole ratio was 43 to 57. Subsequently additions of pure $SbCl_5$ were made but the molar concentration of $Sb^{+3}$ present in the mixture comprising that added plus that formed, was always in excess of the molar concentration of $Sb^{+5}$. Weighing and surface loss calculation show the following corrosions in mils per year (m p y):
Inconel 600 — 2.9
Nickel 200 — 5.9
316 SS — 3.3
Monel 400 — 13
C-20 Cb3 — 1.4

This shows that the preferred ratio of pentavalent:trivalent antimony did not unduly corrode metals of which reactors are normally constructed.

EXAMPLE 12

The following corrosion studies were carried out in polytetrafluoroethylene bottles at 20° C.:

| Salt Added | Wt. % of salt based on BF | Metal | Corrosion in mils per year |
|---|---|---|---|
| $SbCl_5$ | 25 | 316 ss | too much to measure |
| " | " | Carbon Steel | " |
| " | " | Carpenter 20 | " |
| " | 10 | Lead | " |
| " | " | Silver | " |

-continued

| Salt Added | Wt. % of salt based on BF | Metal | Corrosion in mils per year |
|---|---|---|---|
| $SbF_3$ | 10 | Monel | 6.7 |
| " | " | Carpenter 20 | 6.9 |
| $SbF_3/Br_2$ (5/1 wt.) | 12 | Monel | 7 |
| " | " | Carpenter 20 | 6 |
| $SbCl_5$ | 3 | Monel | 289 |
| " | " | Carpenter 20 | 132 |
| $SbCl_5/SbCl_3$ (50/50 molar) | 10 | Monel | 1.3 |
| " | " | Carpenter 20 | 1.1 |

This study shows that pentavalent antimony salts per se were far more corrosive than trivalent salts and that the equimolar mixture was only minimally corrosive. Aluminum is relatively inert to all of these mixtures.

EXAMPLE 13

TCP (166 g.) was added to a mixture of 13.2 g of $SbF_3$ and 4.5 g of $SbCl_5$ in 680 g of HF in a polytetrafluoroethylene bottle at 16°–19° C. After 18 hours the mixture was converted in part to fluorinated chloropropanes in 99.4% yield.

EXAMPLE 14

In an experiment performed in a manner similar to Example 6, the initial quantity of HF was 30.75 lbs. with 2.79 lbs. of $SbCl_3/SbCl_5$ in the molar ratio 57/43. To this mixture at 50° C, 20 lbs. of TCP was added, then 0.24 lb. of $SbCl_5$ was added followed by 10 lbs. of TCP. The following $SbCl_5$/TCP pound increments were subsequently added as frequently as every two hours:
 0.24/16.25
 0.50/6
 0.50/10
 0.50/15
 1.0/12
There was obtained an essentially quantitative yield of organic material comprising 88.4% TFCP, 8.5% DFCP and 3% MFCP.

EXAMPLE 15

This example shows that fluorination with antimony pentachloride without antimony trichloride produces appreciable quantities of undesired side products, i.e. it effects replacement of hydrogen by chlorine.

Eight pounds of HF was placed in a 4.24 gallon Teflon-lined autoclave equipped with a refrigerant-cooled condenser, Teflon-coated stirrer, and lines for adding to and sampling the contents of the vessel. At ambient temperature, 2.55 lbs., 0.0085 mole, of $SbCl_5$ was added. The pot temperature was maintained at 35° C. and the HCl generated by the fluorination of the $SBCl_5$ salts was removed by distillation. Three pounds, 0.0228 mole, of trichloroethylene was added over a half-hour period during which the mixture was held at a temperature of 30° to 35° C. Thereafter, the temperature of the mixture was held between 21° and 42° C. over a 24 hour period. During this time HCl was distilled out as formed. 2-Chloro-1,1,1-trifluoroethane was then removed from the vessel by distillation and, to the HF and antimony salts remaining in the vessel, was added 4.130 lbs. of HF. Over a 15 minute period 3.19 lbs., 0.0243 mole, of trichloroethylene was added. The temperature was held between 23° and 47° C. for about 4 hours while HCl was removed by distillation. A sample of the organic phase in the vessel showed the following percents of known materials present by gas liquid chromatography:
 $CF_3CH_2Cl$ — 49.2%
 $CF_2ClCH_2Cl$ — 16.6%
 $CF_2ClCHCl_2$ — 16.1%
 $CFCl_2CHCl_2$ — 9.4%
Thus 25.5% of the product had undergone replacement of hydrogen by chlorine on the 2-carbon atom.

EXAMPLE 16

Thirty-three pounds of HF was placed in a jacketed 10 gallon monel autoclave equipped with a column with a refrigerant-cooled condenser, stirrer, and lines for adding to and sampling the contents of the vessel. The HF was heated to 30° C. and then 11 lbs., 0.0368 moles, of $SbCl_5$ was added over a one half-hour period. The vessel was heated and the HCl evolved was removed by distillation. Then, 30 lbs., 0.228 mole, of trichloroethylene was added to the reactor while the mixture was kept at 50° C. and the HCl was distilled out as it was formed. The product was distilled out of the vessel and analysis by gas-liquid chromatography showed 36.3 mole % yield of $CF_3CH_2Cl$ and 100% conversion, 78.0 mole % recovery.

A sample of the dark grey residue recovered from the reactor was shown by analysis to contain: Sb, 91.3%; Cu, 1.89%; Ni, 6.81%. Thus, the reaction, conducted in the absence of $SbCl_3$, resulted in corrosion of the reactor since that was the source of the copper and nickel in the residue.

EXAMPLE 17

In a 1180 ml, 316 stainless steel bomb equipped with a Teflon-coated magnetic stirring bar, water-cooled condenser and a pressure gauge, 22.1 grams of a 50—50 mole % mixture of $SbCl_3$-$SbCl_5$ was placed. Then, 150 grams, 7.5 moles, of HF was charged to the reactor. Following this, 360 grams, 2.67 moles, of $CF_2Cl$—$CH_2Cl$ was added over a two and one half hour period. The temperature was maintained between 42° and 49° C. and the gases evolved were vented through an aqueous KOH solution and a Dry Ice trap. The HCl was collected in the base and the low boiling organic compounds in the trap. A second quantity of $CF_2ClCH_2Cl$ of 326 grams, 2.41 moles, was added rapidly at 53° C. After 23 hours at 56° to 70° C., 12.9 grams, 0.043 mole of $SbCl_5$ was added. The mixture was then maintained at 40°–60° C. for 24 hours. Finally, 131.5 grams, 1.00 mole, of $CCl_2$=CHlH was charged to the apparatus at 43° C. and 1.6 hours later an additional 131.5 grams of $CCl_2$=CClH charged. The temperature of the reactor was held between 50° and 60° C. for 21 hours.

The overall organic recovery, including that remaining in the bomb, gave:

| | moles |
|---|---|
| $CF_3CH_2Cl$ | 4.34 |
| $CF_2ClCH_2Cl$ | 0.99 |
| $CFCl_2CH_2Cl$ | 1.57 |
| $CCl_2$=CHCl | 0.072 |
| | 6.972 | which is an almost quantitative yield of useful material. Only 0.96% of the total organic compound weight was HF at the end.

From the high proportion of $CF_3CH_2Cl$ it it apparent that, had the reaction been continued, an even higher yield would have been obtained since the intermediates were on the way toward the end product with minimal replacement of hydrogen.

EXAMPLE 18

In the same vessel described in Example 17 14.4 g of a 50—50 mole % mixture of SbF$_3$—SbCl$_5$ was charged. Then 206.5 g, 10.33 moles, of HF was added and after heating the bomb to 58° C., 3.19 moles of CCl$_3$CH$_2$Cl was added over a 2.5 hour period. After venting the HCl produced an additional 41.4 g, 0.138 mole, of SbCl$_5$ was charged to the apparatus and the mixture heated to 50° C. and held at that temperature for 7 hours. The organic recovery was 94.3 mole %, and the theoretical yield of CF$_3$CH$_2$Cl was 31.1% and of CF$_2$ClCH$_2$Cl was 57.9%. Again, had the reaction continued longer, the yield to desired end product would have been greater.

EXAMPLE 19

To the apparatus described in Example 17 was added 38.2 g of a 50—50 mole % mixture of SbCl$_3$—SbCl$_5$. Then 9.20 moles of HF was added, followed by 3.82 moles of CCl$_3$CH$_2$Cl over a period of 9 hours at 30°–40° C., while venting the evolved HCl through a dilute aqueous KOH solution and condensing low boiling product in a Dry Ice trap. The mixture was then held at 45° to 50° C. for 45 hours. All the recovered organic materials give the following quantities:

|  | moles |
|---|---|
| CF$_3$CH$_2$Cl | 1.31 |
| CF$_2$ClCH$_2$Cl | 1.95 |
| CF$_2$ClCHCl$_2$ | trace |
| CFCl$_2$CH$_2$Cl | 0.31 |
| CCl$_2$=CHCl | 0.05 |
| CFCl$_2$CHCl$_2$ | 0.01 |
| CCl$_3$CH$_2$Cl | 0.04 |
| CCl$_3$CHCl$_2$ | trace |
| Other | 0.01 |
|  | 3.68 (recovery 96.3%) |

Thus compounds with only one hydrogen atom, i.e. which underwent chlorination rather than merely replacement of chlorine by fluorine, are produced in only minute amounts.

A 316 stainless steel corrosion strip present during this entire run showed a loss of 17 mils/year, i.e. minimal corrosion.

EXAMPLE 20

In an experiment conducted in a similar manner to Example 19 but starting with trichloroethylene, after about 47 hours at 25° to 50° C. there was a quantitative recovery of organic material with the following analysis:

|  | mole % |
|---|---|
| CF$_3$CH$_2$Cl | 3.3 |
| CF$_2$ClCH$_2$Cl | 68.0 |
| CFCl$_2$CH$_2$Cl | 26.7 |
| CCl$_3$CH$_2$Cl | 1.2 |

Again, there was minimal chlorination.

A corrosion strip of Carpenter 20 steel showed a loss of 3.8 mils/year and 316 stainless steel 1.7 mils/year, i.e. minimal corrosion.

EXAMPLE 21

In a reaction similar to Example 20 but where the temperature was kept below 30° C. the conversion was similar to that in Example 20 after 4.5 hours.

EXAMPLE 22

In an experiment similar to Example 21 but using a 67–33 mole % mixture of SbCl$_3$—SbCl$_5$ the product mixture showed low conversion after 24 hours at about 25° C. but a conversion similar to Example 20 after an additional day at about 50° C.

EXAMPLE 23

In the apparatus described in Example 17 the fluorination of 1.11 moles of CHClF$_2$ was conducted using 20.6 g of 50—50 mole % SbCl$_3$—SbCl$_5$ in 7.7 moles of HF at about 25° C. for 47 hours. At that time 52.8% of the starting material had been converted to CHF$_3$.

In a similar manner CCl$_4$ can be fluorinated readily.

EXAMPLE 24

The antimony salts and HF remaining from Example 23 were used to fluorinate 180 g. of benzotrichloride. After about 15 minutes the reactor contents were separated and 119 g. of material analyzing 98.4% benzotrifluoride was recovered.

EXAMPLE 25

In a 4 ounce Teflon bottle containing a Teflon-covered magnetic stirring bar were added 3.0 grams of a 50—50 mole % mixture of SbCl$_3$—SbCl$_5$ and 97 grams of HF. To this was added 13.5 grams of hexachlorometaxylene dissolved in 35.6 grams of dichlorotetrafluoroethane in a period of 45 minutes. After additional 2.25 hours at ambient temperatures all the hexachlorometaxylene was converted to hexafluorometaxylene.

EXAMPLE 26

In the same reactor described in Example 17, 26.9 g of a 50—50 mole % mixture of SbCl$_3$—SbCl$_5$ was placed and 200 g of HF was added. Following this 295 g of 1,1,1-trichloropropane was added over a two-hour period while the temperature was kept below 32° C. After a total of 24 hours an 81% yield of 1,1,1-trifluoropropane was obtained.

It will be appreciated that the instant specification and examples are set forth by way of illustration and not limitation, and that various modifications and changes may be made without departing from the spirit and scope of the present invention.

What is claimed is:

1. In the containing of a mixture of HF and antimony pentahalide in a vessel normally corroded thereby, the improvement which comprises adding thereto antimony trihalide in at least an approximately equimolar amount relative to the pentahalide, whereby corrosion of said vessel is inhibited.

* * * * *

UNITED STATES PATENT AND TRADEMARK OFFICE
CERTIFICATE OF CORRECTION

PATENT NO. : 4,138,355
DATED : February 6, 1979
INVENTOR(S) : Louis L. Ferstandig It is certified that error appears in the above-identified patent and that said Letters Patent are hereby corrected as shown below:

| COLUMN | LINE | | |
|---|---|---|---|
| 1 | 66 | delete "$\leftarrow$" and insert -- $\longrightarrow$ --. | |
| 1 | 66 | insert --$CH_2$- -- after "$F_2ClC$-". | |
| 2 | 1 | delete "$\leftarrow$" and insert -- $\longrightarrow$ --. | |
| 2 | 26 | delete "pentahlide" and insert --pentahalide--. | |
| 2 | 35 | insert --is-- after "it". | |
| 2 | 43 | delete "woul" and insert --would--. | |
| 2 | 47 | delete "35" and insert --85--. | |
| 2 | 61 | delete "Cavlin" and insert --Gavlin--. | |
| 3 | 8 | delete "corresive" and insert --corrosive--. | |
| 3 | 34 | delete "contant" and insert --content--. | |
| 3 | 40 | delete "(HFCP)" and insert --(MFCP)--. | |
| 3 | 46 | delete "step" and insert --stop--. | |
| 3 | 46 | insert --activity-- after "catalytic". | |
| 3 | 52 | delete "(HFCP)" and insert --(MFCP)--. | |
| 3 | 62 | delete "reaction" and insert --reactor--. | |

UNITED STATES PATENT AND TRADEMARK OFFICE
CERTIFICATE OF CORRECTION

PATENT NO. : 4,138,355
DATED : February 6, 1979
INVENTOR(S) : Louis L. Ferstandig It is certified that error appears in the above-identified patent and that said Letters Patent are hereby corrected as shown below:

| COLUMN | LINE | |
|---|---|---|
| 3 | 64 | delete "DPCF" and insert --DFCP--. |
| 7 | 10 | delete "1.3" and insert --1.8--. |
| 8 | 49 | delete "CHIH" and insert --CCIH--. |
| 8 | 66 | delete "it" second occurrence and insert --is-- |

Signed and Sealed this

Eighteenth Day of March 1980

[SEAL]

Attest:

SIDNEY A. DIAMOND

Attesting Officer    Commissioner of Patents and Trademarks